(12) United States Patent
Paul et al.

(10) Patent No.: US 6,554,863 B2
(45) Date of Patent: Apr. 29, 2003

(54) INTERVERTEBRAL ALLOGRAFT SPACER

(75) Inventors: David C. Paul, Phoenixville, PA (US); Hansjuerg W. Emch, Philadelphia, PA (US); Beat Schenk, Nuglar (CH); Joseph A. Yaccarino, III, Somerset, NJ (US)

(73) Assignees: Synthes, Paoli, PA (US); Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 09/899,086

(22) Filed: Jul. 6, 2001

(65) Prior Publication Data

US 2002/0062153 A1 May 23, 2002

Related U.S. Application Data

(63) Continuation of application No. 09/363,844, filed on Jul. 30, 1999, now Pat. No. 6,258,125.
(60) Provisional application No. 60/095,209, filed on Aug. 3, 1998.

(51) Int. Cl.[7] .................................................. A61F 2/44
(52) U.S. Cl. ................................................... 623/17.11
(58) Field of Search ........................... 623/17.11–17.16

(56) References Cited

U.S. PATENT DOCUMENTS

| | | | |
|---|---|---|---|
| 3,848,601 A | 11/1974 | Ma et al. ..................... | 128/305 |
| 4,059,115 A | 11/1977 | Jumashev et al. ........... | 128/317 |
| 4,627,853 A | 12/1986 | Campbell et al. ............. | 623/16 |
| 4,678,470 A | 7/1987 | Nashef et al. ................. | 623/16 |
| 4,781,721 A | 11/1988 | Grundei ........................ | 623/16 |
| 4,834,757 A | 5/1989 | Brantigan ..................... | 623/17 |
| 4,858,603 A | 8/1989 | Clemow et al. ......... | 128/92 ZW |
| 4,877,020 A | 10/1989 | Vich ........................ | 128/92 V |

(List continued on next page.)

FOREIGN PATENT DOCUMENTS

| | | |
|---|---|---|
| DE | 29 10 627 A1 | 9/1980 |
| DE | 42 42 889 A1 | 6/1994 |
| DE | 44 23 257 A1 | 1/1996 |
| DE | 299 13 200 U1 | 10/1999 |
| EP | 0 505 634 A1 | 9/1992 |
| EP | 0 517 030 A2 | 12/1992 |
| EP | 0 538 183 | 4/1993 |
| EP | 0 577 178 A1 | 1/1994 |
| EP | 0 639 351 A2 | 2/1995 |
| EP | 0 646 366 A1 | 4/1995 |
| EP | 0 966 930 A1 | 12/1999 |
| FR | 2 552 659 | 2/1995 |
| FR | 2 717 068 | 9/1995 |
| JP | 6-14947 | 1/1994 |

(List continued on next page.)

OTHER PUBLICATIONS

Fred H. Albee, *Bone Graft Surgery in Disease, Injury and Deformity*, D. Appleton–Century Company, Inc., New York, 1940, pp. 22, 30, 114, 151, 155, 164, 212, 256–257, 311–313.

Fred H. Albee, "Bone Surgery With Machine Tools," *Scientific American*, Apr., 1936, pp. 178–181.

Fred H. Albee, *Bone–Graft Surgery*, W. B. Saunders Company, Philadelphia, Pennsylvania, 1915, pp. 145, 165–166, 171, 368–369.

*Primary Examiner*—David H. Willse
*Assistant Examiner*—Suzette Jackson
(74) *Attorney, Agent, or Firm*—Pennie & Edmonds LLP

(57) ABSTRACT

An allogenic intervertebral implant for fusing vertebrae is disclosed. The implant is a piece of allogenic bone conforming in size and shape with a portion of an end plate of a vertebra. The implant has a wedge-shaped profile to restore disc height and the natural curvature of the spine. The top and bottom surfaces of the implant have a plurality of teeth to resist expulsion and provide initial stability. The implant according to the present invention provides initial stability need for fusion without stress shielding.

20 Claims, 7 Drawing Sheets

U.S. PATENT DOCUMENTS

| | | | |
|---|---|---|---|
| 4,932,973 A | 6/1990 | Gendler | 623/16 |
| 4,936,848 A | 6/1990 | Bagby | 623/17 |
| 4,950,296 A | 8/1990 | McIntyre | 623/16 |
| 4,961,740 A | 10/1990 | Ray et al. | 606/61 |
| 5,026,373 A | 6/1991 | Ray et al. | 606/61 |
| 5,053,049 A | 10/1991 | Campbell | 623/16 |
| 5,062,850 A | 11/1991 | MacMillan et al. | 623/17 |
| 5,092,893 A | 3/1992 | Smith | 623/17 |
| 5,112,354 A | 5/1992 | Sires | 623/16 |
| 5,141,510 A | 8/1992 | Takagi et al. | 623/16 |
| 5,192,327 A | 3/1993 | Brantigan | 623/17 |
| 5,275,954 A | 1/1994 | Wolfinbarger et al. | 436/74 |
| 5,298,254 A | 3/1994 | Prewett et al. | 424/422 |
| 5,306,303 A | 4/1994 | Lynch | 623/16 |
| 5,306,307 A * | 4/1994 | Senter et al. | 623/17.11 |
| 5,306,308 A | 4/1994 | Gross et al. | 623/17 |
| 5,306,309 A | 4/1994 | Wagner et al. | 623/17 |
| 5,320,644 A | 6/1994 | Baumgartner | 623/17 |
| 5,401,269 A * | 3/1995 | Buttner-Janz et al. | 623/17.11 |
| 5,405,391 A | 4/1995 | Hednerson et al. | 623/17 |
| 5,425,772 A | 6/1995 | Brantigan | 623/17 |
| 5,439,684 A | 8/1995 | Prewett et al. | 424/422 |
| 5,443,514 A * | 8/1995 | Steffee | 623/17.11 |
| 5,458,638 A | 10/1995 | Kuslich et al. | 623/17 |
| 5,484,437 A | 1/1996 | Michelson | 606/61 |
| 5,489,307 A | 2/1996 | Kuslich et al. | 623/17 |
| 5,489,308 A | 2/1996 | Kuslich et al. | 623/17 |
| 5,514,180 A * | 5/1996 | Heggeness et al. | 623/17.11 |
| 5,522,899 A | 6/1996 | Michelson | 623/17 |
| 5,534,030 A | 7/1996 | Navarro et al. | 623/17 |
| 5,554,191 A | 9/1996 | Lahille et al. | 623/17 |
| 5,556,379 A | 9/1996 | Wolfinbarger | 604/49 |
| 5,571,190 A | 11/1996 | Ulrich et al. | 623/17 |
| 5,571,192 A | 11/1996 | Schönhöffer | 623/17 |
| 5,591,235 A | 1/1997 | Kuslich | 623/17 |
| 5,593,409 A | 1/1997 | Michelson | 606/61 |
| 5,609,635 A | 3/1997 | Michelson | 623/17 |
| 5,609,636 A | 3/1997 | Kohrs et al. | 623/17 |
| 5,609,637 A | 3/1997 | Biedermann et al. | 623/17 |
| 5,645,598 A | 7/1997 | Brosnahan, III | 623/17 |
| 5,658,337 A | 8/1997 | Kohrs et al. | 623/17 |
| 5,683,394 A | 11/1997 | Rinner | 606/86 |
| 5,683,463 A | 11/1997 | Godefroy et al. | 623/17 |
| 5,683,464 A | 11/1997 | Wagner et al. | 623/17 |
| 5,702,449 A | 12/1997 | McKay | 623/17 |
| 5,702,455 A | 12/1997 | Saggar | 623/17 |
| 5,709,683 A | 1/1998 | Bagby | 606/61 |
| 5,716,415 A | 2/1998 | Steffee | 623/17 |
| 5,722,977 A | 3/1998 | Wilhelmy | 606/84 |
| 5,725,579 A | 3/1998 | Fages et al. | 623/16 |
| 5,728,159 A | 3/1998 | Stroever et al. | 623/16 |
| 5,741,253 A | 4/1998 | Michelson | 606/61 |
| 5,766,252 A | 6/1998 | Henry et al. | 623/17 |
| 5,766,253 A | 6/1998 | Brosnahan, III | 623/17 |
| 5,776,199 A | 7/1998 | Michelson | 623/17 |
| 5,782,830 A * | 7/1998 | Farris | 606/61 |
| 5,785,710 A | 7/1998 | Michelson | 606/61 |
| 5,797,871 A | 8/1998 | Wolfinbarger, Jr. | 604/49 |
| 5,798,096 A | 8/1998 | Pavlyk | 424/78.35 |
| 5,814,084 A | 9/1998 | Grivas et al. | 623/16 |
| 5,820,581 A | 10/1998 | Wolfinbarger, Jr. | 604/49 |
| 5,865,845 A * | 2/1999 | Thalgott | 623/17.11 |
| 5,865,848 A | 2/1999 | Baker | 623/17 |
| 5,885,299 A | 3/1999 | Winslow et al. | 606/99 |
| 5,888,222 A | 3/1999 | Coates et al. | 623/17 |
| 5,888,224 A | 3/1999 | Beckers et al. | 623/17 |
| 5,888,227 A | 3/1999 | Cottle | 623/17 |
| 5,895,426 A | 4/1999 | Scarborough et al. | 623/17 |
| 5,897,593 A | 4/1999 | Kohrs et al. | 623/17 |
| 5,899,939 A * | 5/1999 | Boyce et al. | 623/16.11 |
| 5,899,941 A | 5/1999 | Nishijima et al. | 623/17 |
| 5,904,719 A | 5/1999 | Errico et al. | 623/17 |
| 5,910,315 A | 6/1999 | Stevenson et al. | 424/422 |
| 5,968,098 A | 10/1999 | Winslow | 623/17 |
| 5,972,368 A | 10/1999 | McKay | 424/423 |
| 5,976,187 A | 11/1999 | Richelsoph | 623/17 |
| 5,984,922 A * | 11/1999 | McKay | 606/61 |
| 5,984,967 A * | 11/1999 | Zdeblick et al. | 623/17.11 |
| 5,989,289 A | 11/1999 | Coates et al. | 623/17 |
| 6,008,433 A | 12/1999 | Stone | 623/16 |
| 6,025,538 A | 2/2000 | Yaccarino, III | 623/16 |
| 6,033,438 A | 3/2000 | Bianchi et al. | 623/17 |
| 6,039,762 A | 3/2000 | McKay | 623/17 |
| 6,045,579 A | 4/2000 | Hochshuler et al. | 623/17 |
| 6,045,580 A | 4/2000 | Scarborough et al. | 623/17 |
| 6,059,790 A | 5/2000 | Sand et al. | 606/99 |
| 6,080,158 A | 6/2000 | Lin | 606/61 |
| 6,080,193 A | 6/2000 | Hochshuler et al. | 623/17 |
| 6,090,998 A | 7/2000 | Grooms et al. | 623/16 |
| 6,096,080 A | 8/2000 | Nicholson et al. | 623/17 |
| 6,096,081 A | 8/2000 | Grivas et al. | 623/17.11 |
| 6,111,164 A | 8/2000 | Rainey et al. | 623/16 |
| 6,143,033 A * | 11/2000 | Paul et al. | 623/17.11 |
| 6,187,329 B1 | 2/2001 | Agrawal et al. | 424/426 |
| 6,200,347 B1 * | 3/2001 | Anderson et al. | 623/16.11 |
| 6,206,923 B1 | 3/2001 | Boyd et al. | 623/17.11 |
| 6,241,769 B1 | 6/2001 | Nicholson et al. | 623/17.11 |
| 6,245,108 B1 | 6/2001 | Biscup | 623/17.11 |
| 6,258,125 B1 * | 7/2001 | Paul et al. | 623/17.11 |
| 6,261,586 B1 | 7/2001 | McKay | 424/423 |
| 6,270,528 B1 | 8/2001 | McKay | 623/17.11 |
| 6,277,149 B1 * | 8/2001 | Boyle et al. | 623/17.16 |
| 6,371,988 B1 * | 4/2002 | Pafford et al. | 623/17.11 |
| 2001/0001129 A1 | 5/2001 | McKay et al. | 623/17.16 |
| 2001/0010021 A1 | 7/2001 | Boyd et al. | 623/17.13 |
| 2001/0014831 A1 | 8/2001 | Scarborough | 623/23.51 |
| 2001/0016775 A1 | 8/2001 | Scarborough et al. | 623/17.16 |
| 2001/0016777 A1 | 8/2001 | Biscup | 623/17.16 |
| 2002/0091447 A1 | 7/2002 | Shimp et al. | 623/17.16 |
| 2002/0106393 A1 | 8/2002 | Bianchi et al. | 424/423 |
| 2002/0107570 A1 | 8/2002 | Sybert et al. | 623/13.17 |

FOREIGN PATENT DOCUMENTS

| | | |
|---|---|---|
| WO | WO 94/26213 | 11/1994 |
| WO | WO 95/08964 | 4/1995 |
| WO | WO 95/15133 | 6/1995 |
| WO | WO 96/11642 | 4/1996 |
| WO | WO 96/39988 | 12/1996 |
| WO | WO 97/14378 | 4/1997 |
| WO | WO 97/15248 | 5/1997 |
| WO | WO 97/25945 | 7/1997 |
| WO | WO 97/32547 | 9/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09914 | 3/1999 |
| WO | WO 99/13806 | 3/1999 |
| WO | WO 99/29271 | 6/1999 |
| WO | WO 99/32055 | 7/1999 |
| WO | WO 99/38461 | 8/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/40179 | 7/2000 |
| WO | WO 00/41654 | 7/2000 |
| WO | WO 00/42954 | 7/2000 |
| WO | WO 00/59412 | 10/2000 |
| WO | WO 00/74607 | 12/2000 |
| WO | WO 00/74608 | 12/2000 |
| WO | WO 01/08611 A1 | 2/2001 |

* cited by examiner

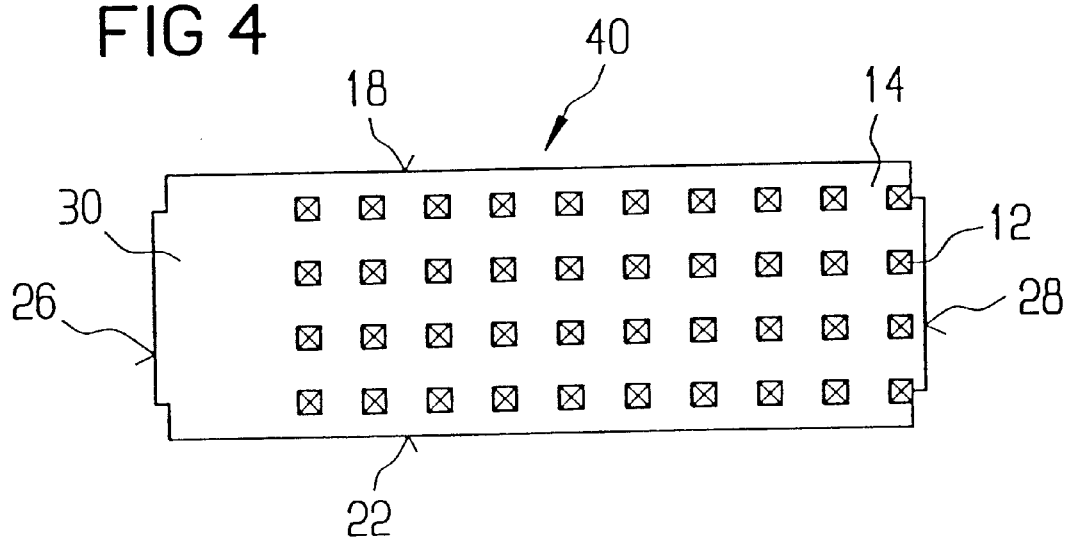
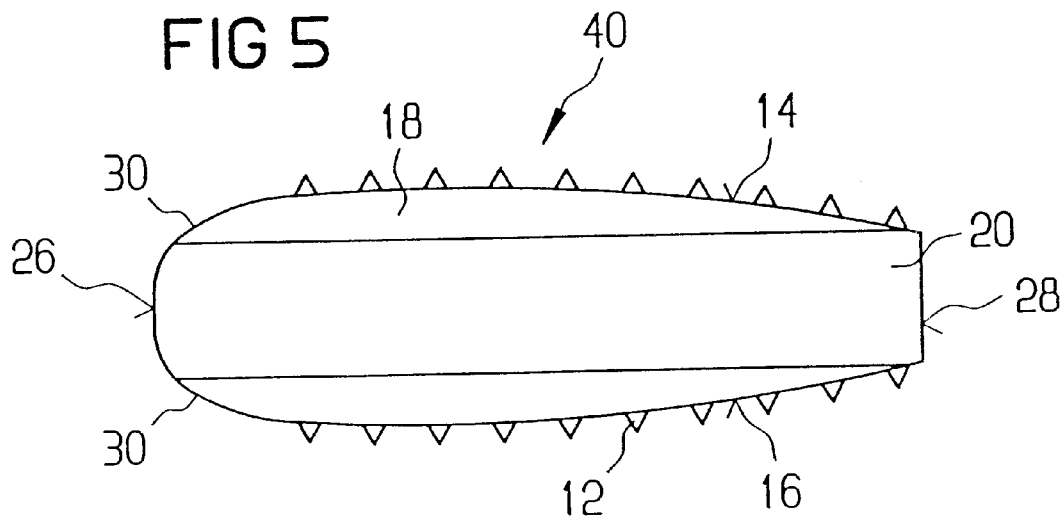

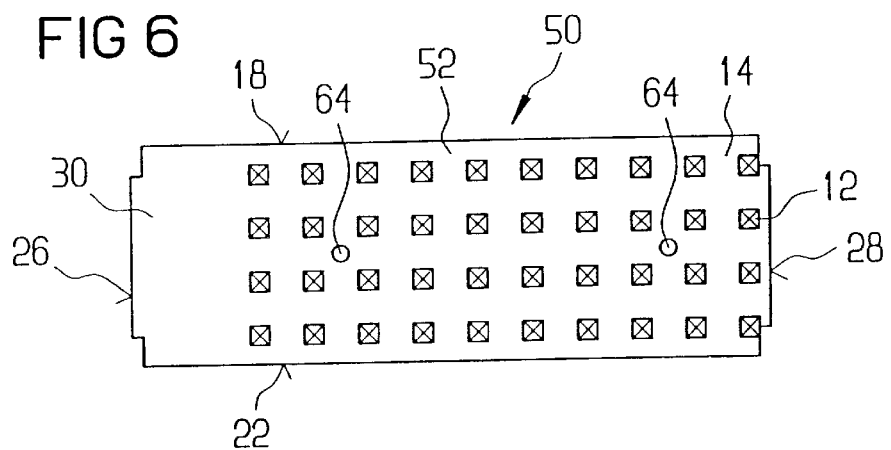
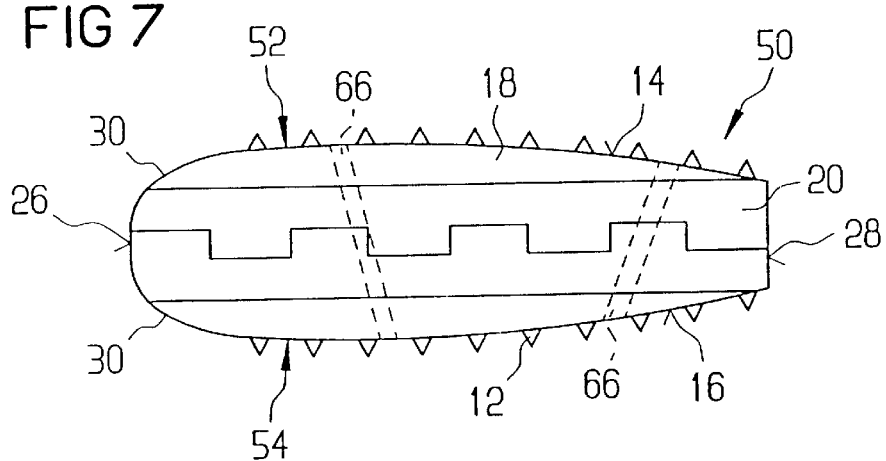
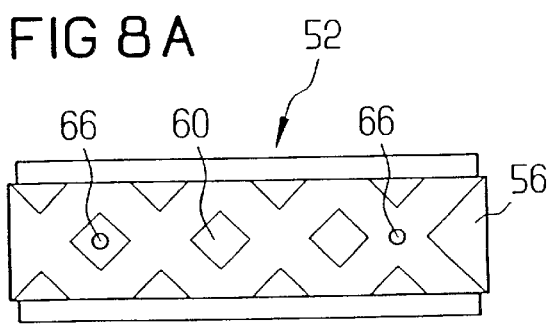
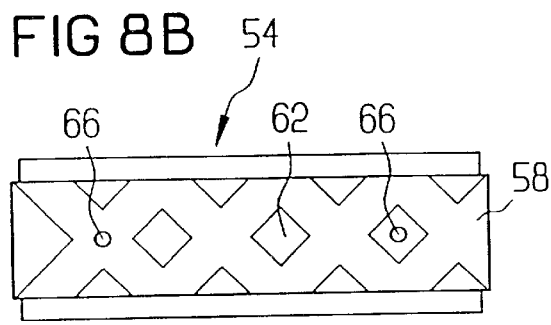

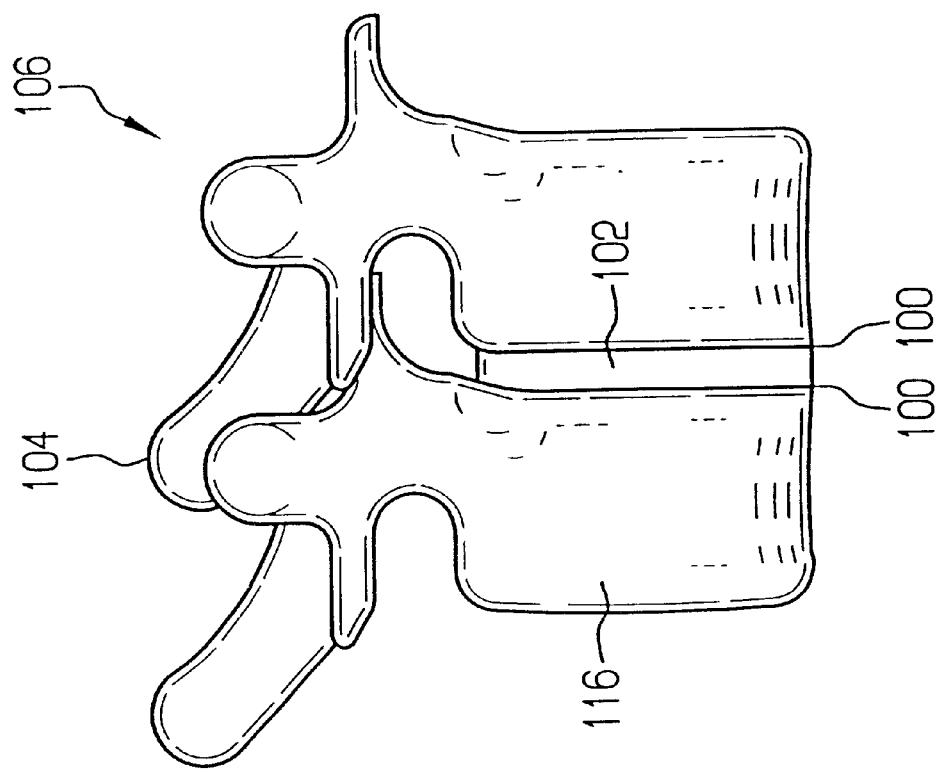
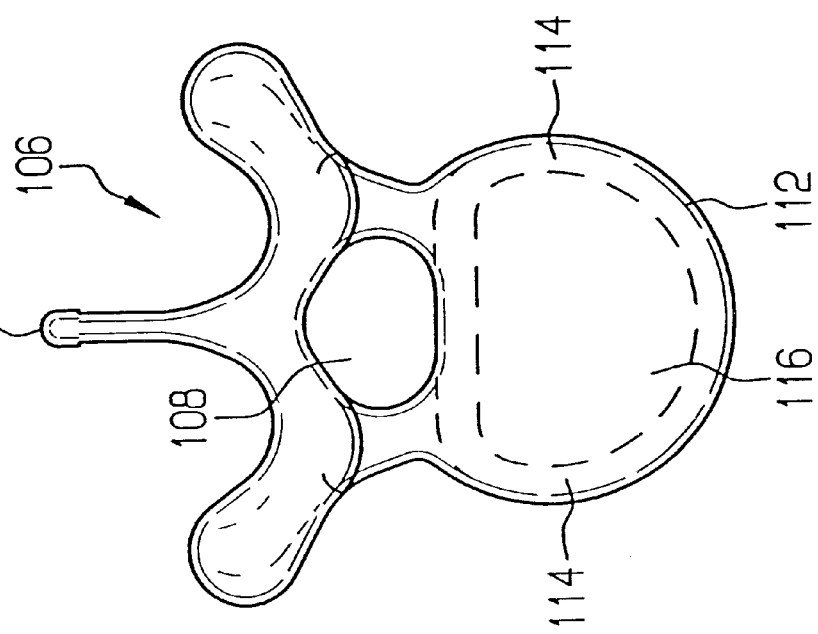

INTERVERTEBRAL ALLOGRAFT SPACER

This application is a continuation of application Ser. No. 09/363,844, filed Jul. 30, 1999, now U.S. Pat. No. 6,258, 125, which claims the benefit of Provisional application Ser. No. 60/095,209, filed Aug. 3, 1998.

FIELD OF THE INVENTION

The present invention is directed to an allogenic implant and, more particularly, to an allogenic intervertebral implant.

BACKGROUND OF THE INVENTION

A number of medical conditions such as compression of spinal cord nerve roots, degenerative disc disease, and spondylolisthesis can cause severe low back pain. Intervertebral fusion is a surgical method of alleviating low back pain. In posterior lumbar interbody fusion ("PLIF"), two adjacent vertebral bodies are fused together by removing the affected disc and inserting an implant that would allow for bone to grow between the two vertebral bodies to bridge the gap left by the disc removal.

A number of different implants and implant materials have been used in PLIF with varying success. Current implants used for PLIF include threaded titanium cages and allografts. Threaded titanium cages suffer from the disadvantage of requiring drilling and tapping of the vertebral end plates for insertion. In addition, the incidence of subsidence in long term use is not known. Due to MRI incompatibility of titanium, determining fusion is problematic. Finally, restoration of lordosis, i.e., the natural curvature of the lumbar spine is very difficult when a cylindrical titanium cage is used.

Allografts are sections of bone taken from a long bone of a donor. A cross section of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They are also MRI compatible so that fusion can be more accurately ascertained and promote the formation of bone, i.e., osteoconductive. Although the osteoconductive nature of the allograft provides a biological interlocking between the allograft and the vertebrae for long term mechanical strength, initial and short term mechanical strength of the interface between the allograft and the vertebrae are lacking as evidenced by the possibility of the allograft being expelled after implantation.

Currently commercially available allografts are simply sections of bone not specifically designed for use in PLIF. As a result, the fusion of the vertebral bodies does not occur in optimal anatomical position. A surgeon may do some minimal intraoperative shaping and sizing to customize the allograft for the patient's spinal anatomy. However, significant shaping and sizing of the allograft is not possible due to the nature of the allograft. Even if extensive shaping and sizing were possible, a surgeon's ability to manually shape and size the allograft to the desired dimensions is severely limited.

Most PLIF implants, whether threaded cages or allograft, are available in different sizes and have widths that vary with the implant height. For example, the width of a cylindrical cages will be substantially equivalent to the height. Although larger heights may be clinically indicated, wider implants are generally not desirable since increased width requires removal of more of the facet, which can lead to decreases stability, and more retraction of nerve roots, which can lead to temporary or permanent nerve damage.

As the discussion above illustrates, there is a need for an improved implant for fusing vertebrae.

SUMMARY OF THE INVENTION

The present invention relates to an allogenic intervertebral implant for use when surgical fusion of vertebral bodies is indicated. The implant comprises a piece of allogenic bone conforming in size and shape with a portion of an end plates of the vertebrae and has a wedge-shaped profile with a plurality of teeth located on top and bottom surfaces. The top and bottom surfaces can be flat planar surfaces or curved surfaces to mimic the topography of the end plates. The implant has a channel on at least one side for receiving a surgical tool. This channel runs in the anterior direction to accommodate a variety of surgical approaches. A threaded hole on the anterior, posterior, posterior-lateral, or lateral side can be provided for receiving a threaded arm of an insertion tool.

In another embodiment, the implant has an interior space for receiving an osteoconductive material to promote the formation of new bone.

In another embodiment, the implant is made of a plurality of interconnecting sections with mating sections. Preferably, the implant is made in two halves: a top portion having a top connecting surface and a bottom portion having a bottom connecting surface. The top connecting surface mates with the bottom connecting surface when the top and bottom portions are joined. The top and bottom portions have holes that align for receiving a pin to secure the top and bottom portions together. The pin can be made of allogenic bone.

In a different embodiment, the medial side of the implant has a scalloped edge such that when a first implant is implanted with a second implant with the medial sides facing each other, the scalloped edges define a cylindrical space.

The present invention also relates to a discrete spacer used in conjunction with any of the other embodiments of the implant. The spacer comprises a piece of allogenic bone conforming in size and shape with a portion of an end plates of the vertebrae and has a wedge-shaped profile with substantially smooth top and bottom surfaces. The intersecting regions between the top and bottom surfaces and at least one of the lateral sides and the intersecting regions between the anterior and posterior sides and the same lateral side are carved surfaces to facilitate implantation of the spacer. Thus, the spacer can be implanted through an opening on one side of the spinal canal and moved with a surgical instrument to the contralateral side.

BRIEF DESCRIPTION OF THE DRAWINGS

FIG. 4 is a top view of a second embodiment of the implant;

FIG. 5 is a side view of the implant of FIG. 4;

FIG. 6 is a top view of a third embodiment of the implant;

FIG. 7 is a side view of the implant of FIG. 6;

FIG. 8A is a top view of a top connecting surface of a top portion of the implant of FIG. 6;

FIG. 8B is a top view of a bottom connecting surface of a bottom portion of the implant of FIG. 6;

FIG. 12 is a top view of a vertebral bone characteristic of those of the cervical, thoracic, and lumbar spine;

FIG. 13 is a side view of sequentially aligned vertebral bones, such as are found in the cervical, thoracic, or lumbar spine;

DESCRIPTION OF THE PREFERRED EMBODIMENTS

Figure 1:
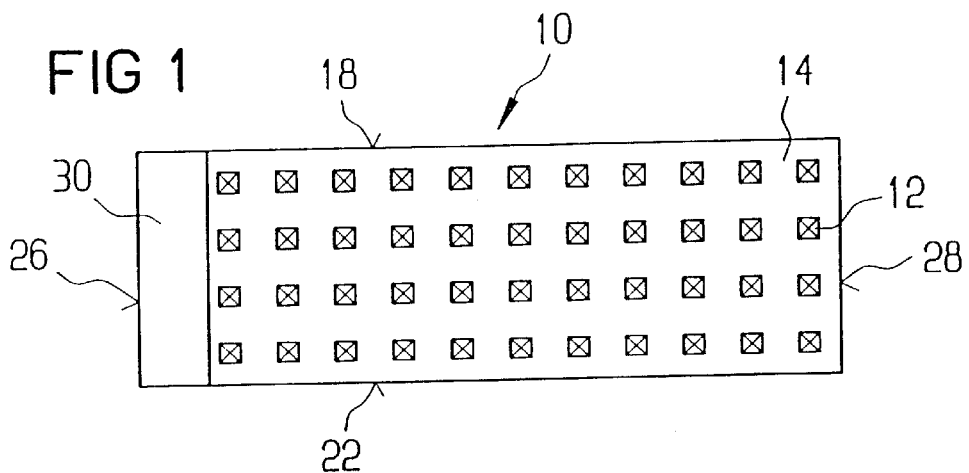
FIG. 1 is a top view of a first embodiment of the implant according to the present invention.
Figure 10A:
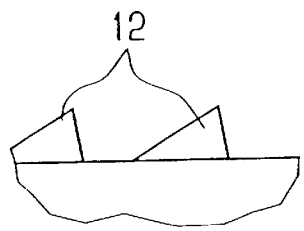
FIG. 10A is a side view of one embodiment of the teeth on the implant.
Figure 10B:
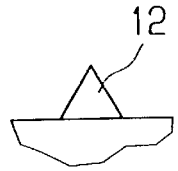
FIG. 10B is a side view of a second embodiment of the teeth of the implant.

FIG. 1 shows a top view of a first embodiment of intervertebral allograft spacer or implant 10 according to the present invention. Implant 10 conforms in size and shape with a portion of end plates of the vertebrae between which implant 10 is to be implanted. Because implant 10 is an allograft, implant 10 promotes the formation of new bone to fuse the two vertebral bodies together. Although implant 10 will probably be predominantly used in the lumbar region of the spine, implant 10 can be configured for implantation in any region of the spine. Implant 10 has a plurality of teeth 12 on superior and inferior surfaces 14, 16 which provide a mechanical interlock between implant 10 and the end plates. Teeth 12 provide the mechanical interlock by penetrating the end plates. The initial mechanical stability afforded by teeth 12 minimizes the risk of post-operative expulsion of implant 10. Teeth 12 can be pyramid-shaped (FIG. OA). Preferably, the angle formed from the tip to the base is approximately 60°. Alternatively, teeth 12 have a saw tooth shape with the saw tooth running in the anterior-posterior direction (FIG. 10B).

Figure 2:
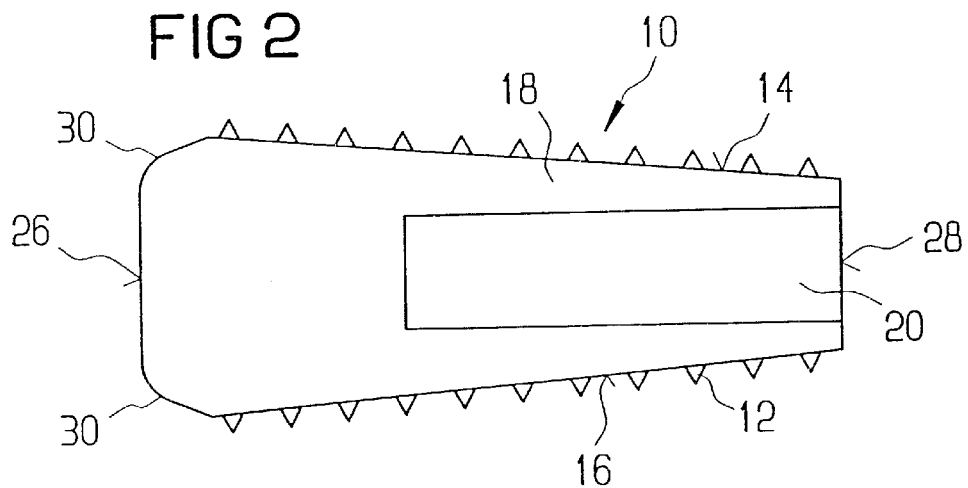
FIG. 2 is a side view of the implant of FIG. 1.
Figure 3:
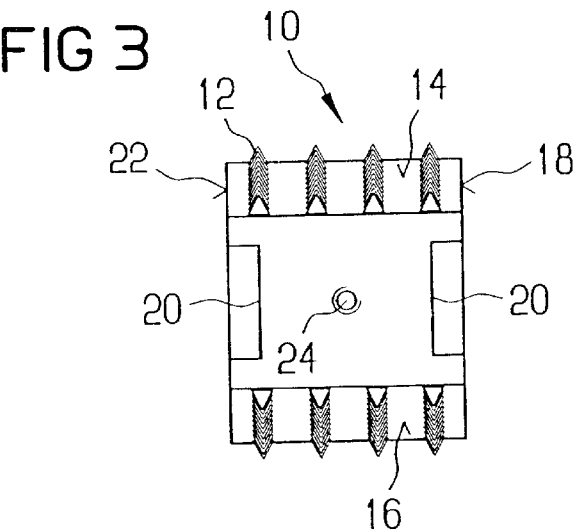
FIG. 3 is a back view of the implant of FIG. 1.
Figure 9:
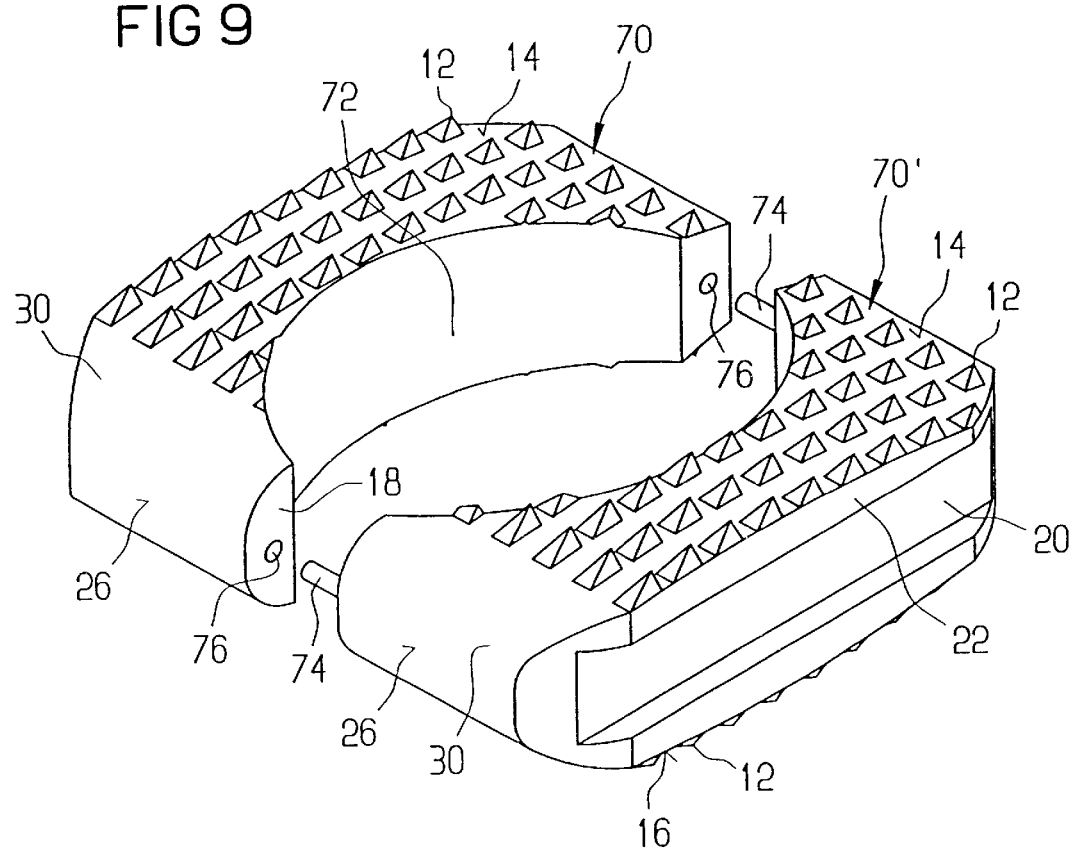
FIG. 9 is a perspective view of a fourth embodiment of the implant.

As shown in FIG. 2 and FIG. 3, a first lateral side 18 has a channel 20 and a second lateral side 22 also has a channel 20. Channels 20 are sized to receive a surgical instrument such as an inserter for implantation of implant 10. If the inserter has a threaded arm, implant 10 can be provided with a threaded hole 24. In FIG. 2, channel 20 is shown extended only partially along first lateral side 18. Channel 20 can extend along the entire length of first lateral side 18 as shown in the embodiment of FIG. 5. In FIG. 3, channels 20 are shown on both first and second lateral sides 18, 22. It should be noted that implant 10 can also have no channels or channels on one lateral side only as shown in the embodiment of FIG. 9.

The dimensions of implant 10 can be varied to accommodate a patient's anatomy. Typically, implant 10 would have a width between 6–15 mm (in the medial-lateral direction), a length between 15–30 mm (in the anterior-posterior direction), and a height between 4–30 mm (maximum height in the superior-inferior direction). The size of implant 10 allows implant 10 to be implanted using conventional open surgical procedures or minimally invasive procedures, such as laparoscopic surgery. Additionally, because the width is kept to a restricted size range and does not necessarily increase with implant height, taller implants can be used without requiring wider implants. Thus, facet removal and retraction of nerve roots can remain minimal.

In order to restore the natural curvature of the spine after the affected disc has been removed, implant 10 has a wedge-shaped profile. As shown in FIG. 2, this wedge shape results from a gradual decrease in height from an anterior side 26 to a posterior side 28. In anatomical terms, the natural curvature of the lumbar spine is referred to as lordosis. When implant 10 is to be used in the lumbar region, the angle formed by the wedge should be approximately between 4.2° and 15° so that the wedge shape is a lordotic shape which mimics the anatomy of the lumbar spine.

In order to facilitate insertion of implant 10, anterior side 26 transitions to superior and inferior surfaces 14, 16 with rounded edges 30. Rounded edges 30 enable implant 10 to slide between the end plates while minimizing the necessary distraction of the end plates.

Although implant 10 is typically a solid piece of allogenic bone, implant 10 can be provided with a hollow interior to form an interior space. This interior space can be filled with bone chips or any other osteoconductive material to further promote the formation of new bone.

FIG. 4 shows a top view of a second embodiment of an implant 40 according to the present invention. In general, most of the structure of implant 40 is like or comparable to the structure of implant 10. Accordingly, discussion of the like components is not believed necessary. The superior and inferior surfaces 14, 16 of implant 10 are flat planar surfaces. As seen best in FIG. 5, superior and inferior surfaces 14, 16 of implant 40 are curved surfaces which still retain the wedge-shaped profile. The curved surfaces of superior and inferior surfaces 14, 16 of implant 40 are a mirror-image of the topography of the vertebral end plates. Thus, the curved surfaces conform to the contours of the end plates.

FIG. 6 shows a top view of a third embodiment of an implant 50 according to the present invention. In general, most of the structure of implant 50 is like or comparable to the structure of implants 10, 40. Accordingly, discussion of the like components is not believed necessary. As best seen in FIG. 7, implant 50 comprises a top portion 52 joined to a bottom portion 54. As it may be difficult to obtain a single section of allogenic bone from which implant 50 is to be made, fabricating implant 50 in two pieces, i.e. top and bottom portions 52, 54, allows smaller sections of allogenic bone to be used. A top connecting surface 56 and a bottom connecting surface 58 define the interface between top and bottom portions 52, 54. As shown in FIGS. 8A and 8B, top and bottom surfaces 56, 58 have ridges 60 that mate with grooves 62 to interlock top and bottom portions 52, 54. Preferably, ridges 60 and grooves 62 are formed by milling top and bottom surfaces 56, 58 in a first direction and then milling a second time with top and bottom surfaces 56, 58 oriented 90° with respect to the first direction.

A pin 64 passing through aligned holes 66 in top and bottom portions 52, 54 serves to retain top and bottom portions 52, 54 together. Although pin 64 can be made of any biocompatible material, pin 64 is preferably made of allogenic bone. The number and orientation of pins 64 can be varied.

Figure 11:
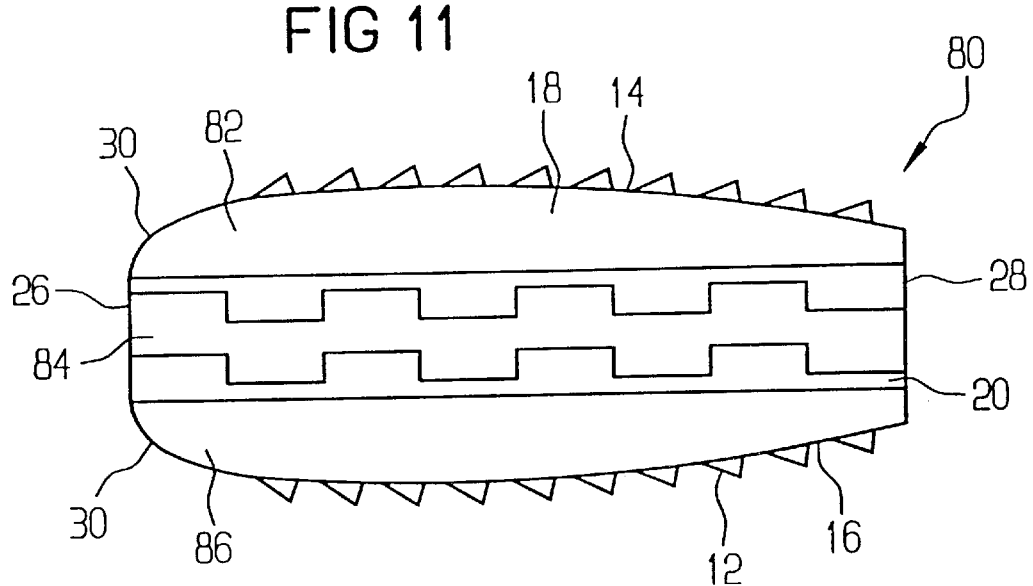
FIG. 11 is a side view of an embodiment of the implant similar to the embodiment of FIGS. 6–8.

FIG. 11 shows an embodiment of an implant 80 which, like implant 50, is made in multiple pieces. In general, most of the structure of implant 80 is like or comparable to the structure of implants 10, 40, 50. Accordingly, discussion of the like components is not believed necessary. Implant 80 has a top portion 82, a middle portion 84, and a bottom portion 86. As was the case for implant 80, the surfaces between the portions are mating surfaces with interlocking surface features, such as ridges and grooves. One or more pins preferably hold top, middle, and bottom portions 82, 84, 86 together.

FIG. 9 shows a perspective view of a fourth embodiment of a first implant 70 according to the present invention. A second implant 70', which is substantially similar to first implant 70, is also shown. In general, most of the structure of first and second implants 70, 70' is like or comparable to the structure of implants 10, 40, 50. Accordingly, discussion of the like components is not believed necessary. First lateral sides 18 of first and second implants 70, 70' are scalloped to have a C-shape. When first and second implants 70, 70' are placed side by side with the first lateral sides 18 facing each other, a cylindrical space 72 is formed. When first and second implants 70, 70' are implanted together, cylindrical space 72 can be filled with osteoconductive material to help promote the formation of new bone. First and second implants 70, 70' can be provided with locking pins 74 which engage apertures 76 to maintain the spatial relationship between first and second implants 70, 70'.

Figure 14:
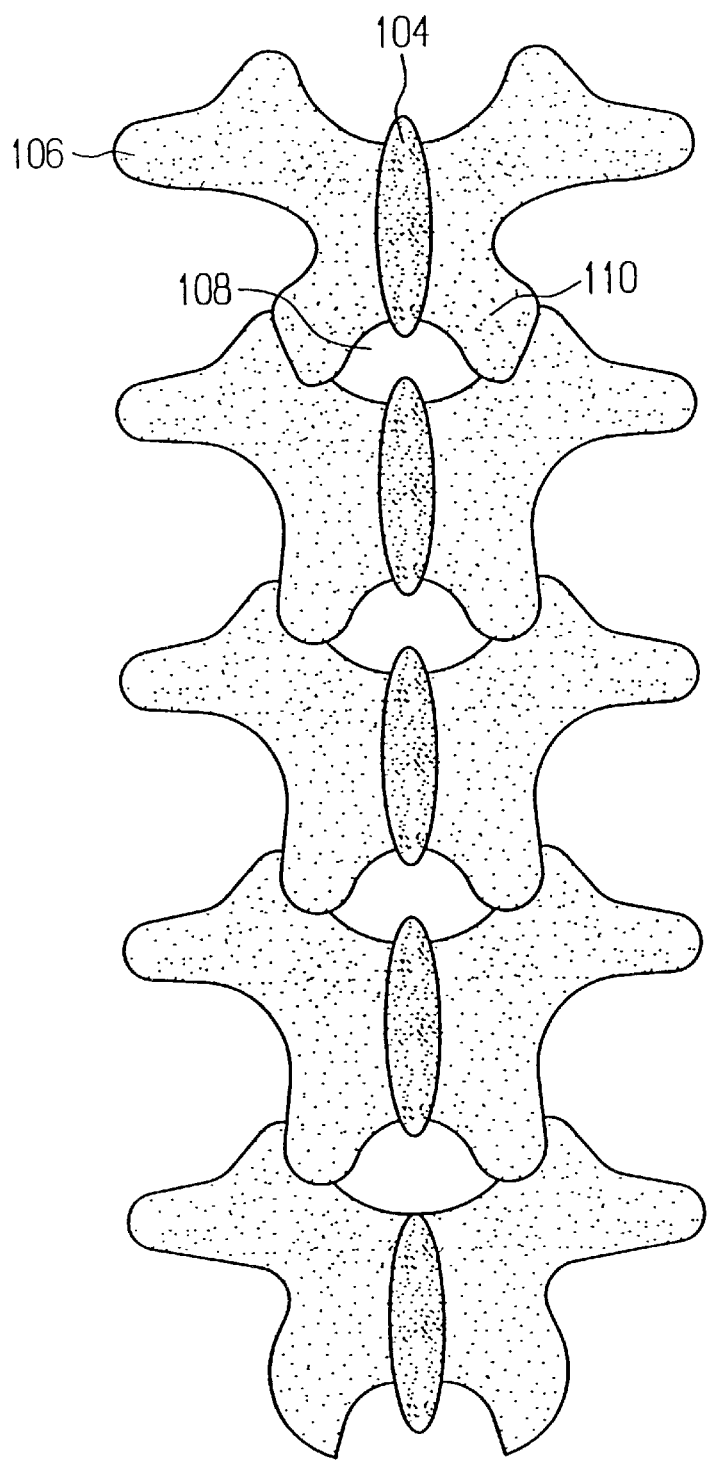
FIG. 14 is a posterior view of a sequence of vertebrae.

The use of the implant according to the present invention will now be described with reference to FIGS. 12–14 and using posterior lumbar interbody fusion as an example. As the implant according to the present invention conforms in size and shape to a portion of end plates 100, preoperative planning is recommended for proper sizing. Determine the appropriate implant height by measuring adjacent intervertebral discs 102 on a lateral radiograph. The implant must be seated firmly with a tight fit between end plates 100 when the segment is fully distracted. The tallest possible implant should be used to maximize segmental stability. Due to variability in degrees of magnification from radiographs, the measurements are only an estimate.

With the patient in a prone position on a lumbar frame, radiographic equipment can assist in confirming the precise intraoperative position of the implant. The surgeon incises and dissects the skin from the midline laterally and locates spinous process 104, lamina 106, dura 108, and nerve roots of the appropriate level(s). As much as facets 110 as possible should be preserved to provide stability to the intervertebral segment. The surgeon performs a laminotomy to the medial aspect of facet 110 and reflects dura 108 to expose an approximately 13 mm window to the disc space. Disc 102 is removed through the window until only anterior 112 and lateral 114 annulus remain. The superficial layers of the entire cartilaginous end plates 100 are also removed to expose bleeding bone. Excessive removal of the subchondral bone may weaken the anterior column. Furthermore, if the entire end plate is removed, this may result in subsidence and a loss of segmental stability.

Distraction can be done with either a surgical distractor or a trial spacer implant. In the first method, the distractor blades are placed into the disc space lateral to dura 108. The curve on the neck of the distractor should be oriented toward the midline. The distractor blades should be completely inserted into the disc space so that the ridges at the end of the blades rest on vertebral body 116. Fluoroscopy can assist in confirming that the distractor blades are parallel to end plates 100. Correct placement will angle the handles of the distractor cranially. particularly at L5–S1. The handle of the distractor is squeezed to distract the innerspace. The distraction is secured by tightening the speed nut on the handle.

Using the preoperatively determined size, a trial spacer is inserted in the contralateral disc space with gentle impaction. Fluoroscopy and tactile judgement can assist in confirming the fit of the trial spacer until a secure fit is achieved. Using either the slots or threader hole on the implant, the selected implant is inserted in the contralateral disc space. Alternatively, the channels on the implant allow distraction and insertion to occur on the same side. Regardless of the side the implant is inserted in, autogenous cancellous bone or a bone substitute should be placed in the anterior and medial aspect of the vertebral disc space prior to placement of the second implant. The distractor is removed and a second implant of the same height as the first implant is inserted into the space, using gentle impaction as before. Preferably, the implants are recessed 2–4 mm beyond the posterior rim of the vertebral body.

Figure 15:
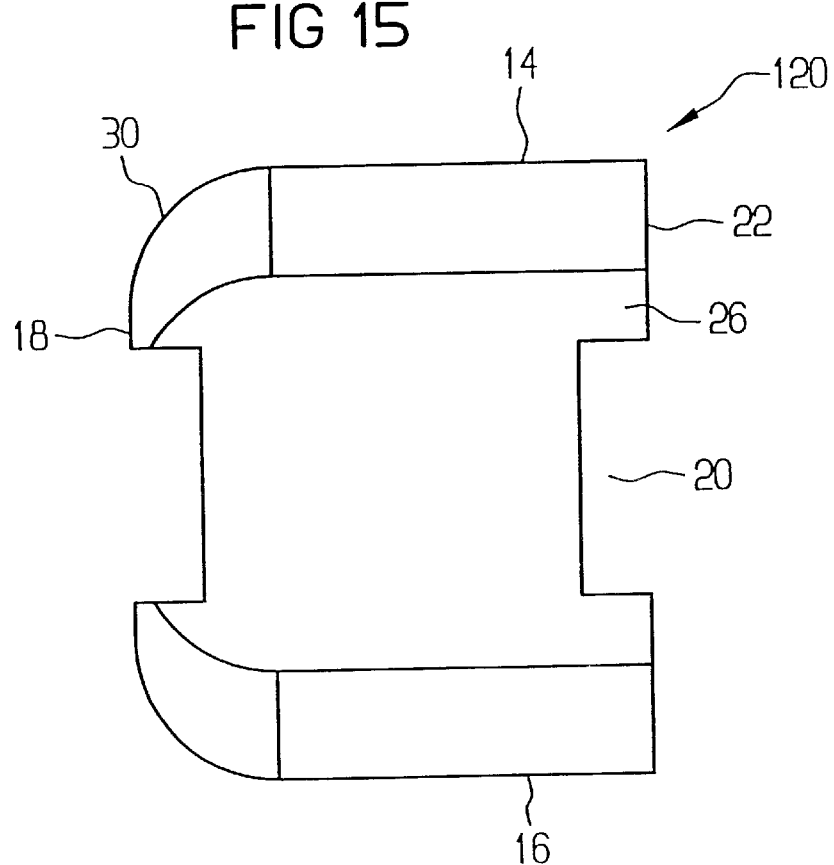
FIG. 15 is an end view of another embodiment of the implant.

As previously noted, the implant according to the present invention can be inserted using minimally invasive procedures. In some of these procedures, only one side of the spinal cord needs to be approached. This minimizes muscle stripping, scar tissue in the canal, and nerve root retraction and handling. In clinical situations in which bilateral implant placement is required, proper implantation on the side opposite the incision can be difficult. FIG. 15 shows a beveled spacer 120 that facilitates placement on the side contralateral to the incision. In general and unless otherwise described, most of the structure of beveled spacer 120 is like or comparable to the structure of implants 10, 40, 50, and 80. Accordingly, discussion of the like components is not believed necessary. First lateral side 18 transitions to superior and inferior surfaces 14, 16 with rounded edges 30. First lateral side 18 also transitions to anterior and posterior sides 26, 28 with rounded edges 30. Additionally, spacer 120 has no teeth. The lack of teeth and rounded edges 30 enable spacer 120 to slide between the end plate and across the evacuated disc space (from one lateral annulus to the other) to the contralateral side. As first lateral side 18 is the side that must promote movement of spacer 120, the use of rounded edges 30 on second lateral side 22 is optionally. Once spacer 120 has been placed on the side contralateral to the single incision using a surgical instrument to push spacer 120, bone graft or other osteoconductive material is packed in the disc space. Finally, an implant (any of implant 10, 40, 50, 70, or 70' can be used) is implanted in the side proximal to the incision.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An intervertebral implant comprising: a piece of allogenic bone conforming in size and shape with a portion of an end plate of a vertebra and having a wedge-shaped profile, wherein top and bottom surfaces of the implant have a plurality of teeth, wherein the implant further comprises a top portion having a top connecting surface and a bottom portion having a bottom connecting surface, the top connecting surface mating with the bottom connecting surface when the top and bottom surfaces are joined.

2. The implant of claim 1, wherein a pin is inserted through a hole in the top portion and a hole in the bottom portion to secure the top and bottom portions together.

3. The implant of claim 2, wherein the pin is made of allogenic bone.

4. The implant of claim 2, wherein the pin intersects the top and bottom connecting surfaces at oblique angles.

5. The implant of claim 1, wherein the implant is made of a plurality of interconnecting sections with mating surfaces.

6. The implant of claim 1, wherein at least one side has a channel for receiving a surgical instrument.

7. The implant of claim 1, wherein the teeth have a pyramid shape.

8. The implant of claim 1, wherein the teeth have a saw tooth shape.

9. The implant of claim 1, wherein at least one side of the implant has at least one hole for attachment of an inserter.

10. The implant of claim 1, wherein the top and bottom surfaces are defined by flat planar surfaces.

11. The implant of claim 10, wherein a region between the top and bottom surfaces and an anterior side of the implant is a curved edge to facilitate implantation of the implant.

12. The implant of claim 1, wherein the top and bottom surfaces are defined by curved surfaces, said curved surfaces contoured to mimic surfaces of the end plates of the vertebrae.

13. A method for restoring disc height between adjacent vertebrae having facing endplates, the method comprising:
   removing at least a portion of a disc located between the adjacent vertebrae;
   distracting an inner space between the facing endplates; and
   inserting the implant of claim 1 to the distracted inner space.

14. The method of claim 13 comprising measuring a distance between the adjacent vertebrae with a preoperative lateral radiograph to determine an implant height.

15. The method of claim 13 wherein a distractor is used to distract the inner space.

16. The method of claim 15 further comprising inserting a trial spacer implant to determine an implant height.

17. An allogenic intervertebral implant comprising top and bottom surfaces, each the top and bottom surfaces provided with a plurality of teeth;
   a first portion having a first connecting surface;
   a second portion having a second connecting surface; and
   a core having a first mating surface that mates with the first connecting surface and a second mating surface that mates with the second connecting surface to thereby form the allogenic intervertebral implant.

18. The implant of claim 17, wherein the core is made of a single piece of allogenic bone.

19. The implant of claim 17, wherein a pin is inserted through a hole in the first portion, a hole in the core, and a hole in the second portion to secure the core and the first and second portions together.

20. The implant of claim 19, wherein the pin intersects the top and bottom connecting surfaces at oblique angles.

* * * * *

UNITED STATES PATENT AND TRADEMARK OFFICE
CERTIFICATE OF CORRECTION

PATENT NO. : 6,554,863 B2
DATED : April 29, 2003
INVENTOR(S) : Paul et al.

It is certified that error appears in the above-identified patent and that said Letters Patent is hereby corrected as shown below:

Column 7,
Line 26, replace "to" with -- into --;

Column 8,
Line 1, before "comprising" insert -- further --;
Line 8, after "comprising" insert -- : --;
Line 9, after "each" insert -- of --.

Signed and Sealed this

Twelfth Day of August, 2003

JAMES E. ROGAN
*Director of the United States Patent and Trademark Office*